United States Patent [19]

Koseki et al.

[11] Patent Number: 4,994,585

[45] Date of Patent: Feb. 19, 1991

[54] METHOD OF PREPARING (S)-γ-HYDROXYMETHYL-α, β-BUTENOLIDE

[75] Inventors: Koshi Koseki; Takashi Ebata; Hiroshi Kawakami; Hajime Matsushita, all of Yokohama; Kazuo Itoh; Yoshitake Naoi, both of Tokyo, all of Japan

[73] Assignees: Japan Tabacco Inc.; Yuki Gosei Kogyo Co., Ltd., both of Tokyo, Japan

[21] Appl. No.: 550,509

[22] Filed: Jul. 10, 1990

[30] Foreign Application Priority Data

Jul. 19, 1989 [JP] Japan .................................. 1-184817

[51] Int. Cl.$^5$ ................... C07D 307/28; C07D 311/00
[52] U.S. Cl. ...................................... 549/323; 549/397
[58] Field of Search ......................................... 549/323

[56] References Cited

FOREIGN PATENT DOCUMENTS 2234077  4/1986  Japan .................... 549/323

OTHER PUBLICATIONS

Tetrahedron Letters, vol. 38, No. 15, pp. 2395–2401, P. Camps et al.
Tetrahedron Letters, vol. 30, pp. 3547–3552, M. Taniguchi et al.
Carbohydrate Research, 58 (1977) 79–87, F. Shafizadeh et al.
Tetrahedron Letters, vol. 28, No. 20, pp. 2299–2300, J. A. J. M. Vekemans et al.
Synthesis, pp. 834–835 (1984).
Carbohydrate Research, 71 (1979), pp. 169–191, F. Shafizadeh et al.

Primary Examiner—Glennon H. Hollrah
Assistant Examiner—Amelia A. Owens
Attorney, Agent, or Firm—Nixon & Vanderhye

[57] ABSTRACT

A method of preparing (S)-γ-hydroxymethyl-α,β-butenolide includes the step of oxidizing a levoglucosenone with a peracid in an organic solvent. Peracetic acid, metha-chloroperbenzoic acid or magnesium monoperoxyphthalate hexahydrate can be used as the peracid. According to this method, an (S)-γ-hydroxymethyl-α,β-butenolide having high optical purity can be easily prepared from a levoglucosenone as a starting material at a high yield.

5 Claims, No Drawings

METHOD OF PREPARING (S)-γ-HYDROXYMETHYL-α, β-BUTENOLIDE

BACKGROUND OF THE INVENTION

1. Field of the Invention

The present invention relates to a method of preparing an (S)-γ-hydroxymethyl-α-,β-butenolide represented by the following formula:

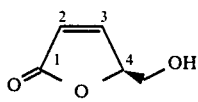

This compound is useful as a starting material for synthesizing medicines such as Burseran and Isostegane which are antileukemic lignans, Lasalocid A which is an antibiotic, and prostaglandine. 2. Description of the Related Art The following two conventional methods for synthesizing (S)-γ-hydroxymethyl-α,β-butenolides are available. These conventional methods, however, have the following problems.

The first method uses a D-ribose as a starting material and synthesizes a subject compound via a ribonolactone, as proposed by P. Camps, et al. (P. Camps et al., Tetrahedron, 38, 2395 (1982)).

According to this method, the product cost is high since ribose as the starting material is expensive.

The second method uses an L-glutamic acid as a starting material and synthesizes a subject compound in six steps in which the starting material is oxidized to the subject compound via a γ-lactone, as proposed by Taniguchi (M. Taniguchi et al., Tetrahedron, 30,3547, (1974)).

The second method which employs a synthesizing process via the γ-lactone has many reaction steps and requires complicated reaction operations. For these reasons, the second method provides a low product yield.

SUMMARY OF THE INVENTION

It is an object of the present invention to provide a method which allows easy preparation of an (S)-γ-hydroxymethyl-α,β-butenolide (to be referred to as a subject compound hereinafter) at low cost.

The present inventors made extensive studies to solve the conventional problems described above, found a method of preparing the subject compound using a levoglucosenone as a starting material, and reached the present invention.

According to the present invention, the above object can be achieved by a method of preparing an (S)-γ-hydroxymethyl-α,β-butenolide, comprising the step of oxidizing a levoglucosenone with a peracid in an organic solvent.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out in the appended claims.

DETAILED DESCRIPTION OF THE PREFERRED EMBODIMENTS

According to the present invention, an oxidation reaction for obtaining subject compound (II) from levoglucosenone (I) is represented as follows:

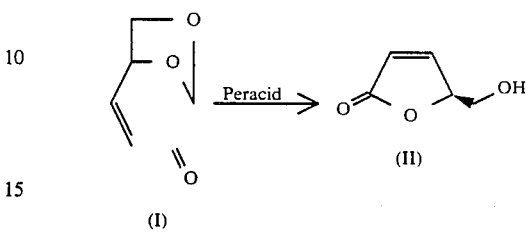

Levoglucosenone (I) used as a starting material is a known material Levoglucosenone (I) can be easily mass-produced by thermally decomposing a cellulose at low cost (F. Shafizadeh, P.S. Chin, Carbohydr.Res., 58, 79, 1977). In addition, according to this method, a pure optical isomer can be prepared.

Examples of the peracid used in oxidation of levoglucosenone (I) in the present invention include peracetic acid, metha-chloroperbenzoic acid, and magnesium monoperoxyphthalate hexahydrate. However, the material as the peracid is not limited to the above materials.

A reaction between levoglucosenone (I) and a peracid is an equimolar reaction Therefore, a sufficient amount of a peracid per mole of the levoglucosenone is theoretically one mole. However, in practice, 1.0 to 3.0 mole of a peracid are preferably used for one mole of a levoglucosenone.

The oxidation reaction in the present invention is carried out in a liquid phase In order to practice the present invention, therefore, a solution of levoglucosenone (I) must be prepared, and a solvent for this solution can be a conventional organic solvent such as acetic acid, methylene chloride, or methanol. In selection of a solvent, it must satisfy the following conditions. Levoglucosenone (I) can be dissolved well in a selected solvent, the selected solvent should not react with a peracid, and a byproduct which disturbs a treatment after the reaction is not produced. Any solvent can be used if it satisfies the above conditions.

The oxidation reaction of levoglucosenone (I) with the peracid can be performed with a very simple operation. More specifically, a peracid is added to a solution of levoglucosenone (I) and is sufficiently reacted with it under stirring at room temperature for one or two days. After the reaction is completed, the peracid left in the reaction mixture is eliminated, and subject compound (II) can be obtained at a high yield.

The resultant subject compound (II) can be directly used as a synthesizing material for medicines and the like. However, subject compound (II) can be purified by silica gel chromatography, as needed, thereby preparing a high-purity subject compound.

The resultant subject compound (II) is not so stable against distillation. Subject compound (II) can be stabilized by acetylation. In order to perform this acetylation, methylene chloride, pyridine, and acetic anhydride are added to subject compound (II) and are reacted under stirring overnight. After the reaction, the reaction solution is washed and dried. The reaction solution is condensed under a reduced pressure and distilled at a high vacuum to obtain acetate subject compound (II).

The method of the present invention will be described in detail by way of its examples.

EXAMPLE 1

10 g (79.4 mmol) of a levoglucosenone were dissolved in 40 ml of acetic acid, and 10.1 ml of 60% peracetic acid were dropped over about 30 minutes. An oxidation reaction was performed under stirring at room temperature for 2 days. After the reaction, 0.5 ml of the reaction solution were sampled, and an amount of peracetic acid left in the solution was quantitatively measured by a potassium iodide/sodium thiosulfate reagent. Based on the measurement, dimethyl sulfide was added to the reaction solution in a molar amount eaqual to the peracetic acid left in the solution and was stirred for an hour, thereby coverting the peracetic acid into acetic acid. The reaction solution was condensed at a reduced pressure, and 100 ml of methanol were added to the condensation residue The resultant mixture was heated up to about 45° to 50° C. and was stirred overnight, thereby converting a formate contained in the mixture (1 to 10%) into a corresponding alcohol which is the subject compound. The mixture was then condensed at a reduced pressure to obtain 9 g of a brown oily product (yield: 99.4%). This oily product was confirmed to be the (S)-γ-hydroxymethyl-α,β-butenolide as the subject compound in accordance with IR and NMR spectra. The IR and NMR spectra are as follows:

IR Spectrum (cm$^{-1}$)

$v_{max}^{film}$: 3450, 1750, 1600

$^1$H-NMR Spectrum (δ/CDCl$_3$)

3.80 (1H, dd, J = 5.0, 12.2 Hz, H-5),
4.00 (1H, dd, J = 3.8, 12.2 Hz, H-5),
5.17 (1H, brs, , H-4),
6.22 (1H, dd, J = 2.1, 5.7 Hz, H-3),
7.49 (1H, dd, J = 1.5, 5.7 Hz, H-2), Reference Example (Acetylation of the Subject Compound)

200 ml of methylene chloride, 7.54 g (95.3 mmol) of pyridine, and 0.73 g (95.3 mmol) of acetic anhydride were added to 9 g of the subject compound prepared in Example 1, and the resultant mixture was stirred overnight at room temperature.

After the reaction, the reaction solution was sequentially washed with 2% hydrochloric acid, water, sodium bicarbonate solution, and sodium chloride solution. The reaction residue was dried with magnesium sulfate anhydride and was condensed at a reduced pressure, thereby eliminating the solvent. The resultant residue was distilled under a vacuum condition and was purified. As a result, 8.01 g of a brown oily product were obtained as an acetylated product (boiling point 96° C./0.3 mmHg) of the subject compound.

The overall yield of this acetylated product from the levoglucosenone was 64.7%, and its physical properties are as follows:

Boiling Point

96° C./0.3 mmHg

Specific Rotation $[α]_D^{23} = -125.6°$

IR Spectrum (cm.$^{-1}$)

$v_{max}^{film}$: 1740(S), 1600, 1230(S)

$^1$H-NMR Spectrum (δ/CDCl$_3$)

2.01 (3H, s, Ac),
4.35 (2H, m, H-5),
5.25 (1H, m, H-4),
6.23 (1H, dd, J = 2.1, 5.8 Hz, H-3),
7.45 (1H, dd, J = 1.6, 5.8 Hz, H-2),

These values of the physical properties coincide with data of the acetylated product of the subject compound described in the paper by Camps et al., as described in the Description of the Related Art. Therefore, the product obtained in Example 1 was confirmed to be the subject compound.

EXAMPLE 2

One gram (7.94 mmol) of a levoglucosenone was dissolved in 9 ml of methylene chloride. To the resultant solution, a suspension obtained by suspending 1.92 g (9.53 mmol) of 85% metha-chloroperbenzoic acid in 15 ml of methylene chloride was added and reacted under stirring at room temperature for two days. A precipitate in the reaction solution was filtered, and the filtrate was condensed. The condensate was purified by silica gel chromatography to obtain 0.27 g of the subject compound (yield 30%).

Physical properties of the subject compound were measured to be as follows:

$^1$H-NMR Spectrum (δ/CDCl$_3$)

3.80 (1H, dd, J = 5.0, 12.2 Hz, H-5),
4.00 (1H, dd, J = 3.8, 12.2 Hz, H-5),
5.17 (1H, brs, H-4),
6.22 (1H, dd, J = 2.1, 5.7 Hz, H-3), The levoglucosenone was confirmed to be converted into the subject compound from the measurement results.

EXAMPLE 3

One gram (7.94 mmol) of a levoglucosenone was dissolved in 8 ml of methanol, and a solution obtained by dissolving 4.72 g (9.53 mmol) of magnesium monoperoxyphthalate hexahydrate into 15 ml of methanol was added thereto and was reacted under stirring at room temperature for one day. The reaction solution was filtered, and the filtrate was condensed to obtain 0.45 g of the subject compound (yield: 50%).

Physical properties of this compound were measured to be as follows:

$^1$H-NMR Spectrum (δ/CDCl$_3$)

3.80 (1H, dd, J = 5.0, 12.2 Hz, H-5),
4.00 (1H, dd, J = 3.8, 12.2 Hz, H-5),
5.17 (1H, brs, H-4),
6.22 (1H, dd, J = 2.1, 5.7 Hz, H-3),
7.49 (1H, dd, J = 1.5, 5.7 Hz, H-2), The levoglucosenone was confirmed to be converted into the subject compound from the measurement results.

According to the present invention, as has been described above in detail, an (S)-γ-hydroxymethyl-α,βbutenolide having high optical purity can be easily manufactured from a levoglucosenone as a starting material at a high yield.

Additional advantages and modifications will readily occur to those skilled in the art. Therefore, the invention in its broader aspects is not limited to the specific details, and illustrated examples shown and described herein. Accordingly, various modifications may be made without departing from the spirit or scope of the general inventive concept as defined by the appended claims and their equivalents.

What is claimed is:

1. A method of preparing (S)-γ-hydroxymethyl-α,β-butenolide, comprising the step of oxidizing a levoglucosenone with a peracid in an organic solvent.

2. A method according to claim 1, wherein the peracid is selected from the group consisting of peracetic acid, metha-chloroperbenzoic acid, and magnesium monoperoxyphthalate hexahydrate.

3. A method according to claim 1, wherein the amount of the peracid is 1.0 to 3.0 mol per mole of the levoglucosenone.

4. A method according to claim 1, wherein the organic solvent is a solvent which can dissolve the levoglucosenone well therein, does not react with the peracid, and does not produce a byproduct which disturbs a treatment after the reaction.

5. A method according to claim 4, wherein the organic solvent is selected from the group consisting of acetic acid, methylene chloride, and methanol

* * * * *

UNITED STATES PATENT AND TRADEMARK OFFICE
CERTIFICATE OF CORRECTION

PATENT NO. : 4,994,585
DATED : February 19, 1991
INVENTOR(S) : Koshi KOSEKI, et al It is certified that error appears in the above-identified patent and that said Letters Patent is hereby corrected as shown below:

Column 2, lines 8-16, change Compound (I) to read as follows:

-- 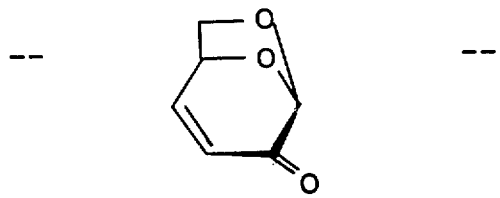 --

(I)

Signed and Sealed this

Third Day of November, 1992

Attest:

DOUGLAS B. COMER

Attesting Officer

Acting Commissioner of Patents and Trademarks